United States Patent
Wen et al.

(10) Patent No.: US 11,884,912 B2
(45) Date of Patent: Jan. 30, 2024

(54) CELL CULTURE DEVICE AND METHOD THEREOF

(71) Applicant: Industrial Technology Research Institute, Hsin-Chu (TW)

(72) Inventors: Kuo-Hsing Wen, Hsinchu County (TW); Ting-Hsuan Chen, Hsinchu County (TW); Cheng-Tai Chen, Taoyuan (TW); Chien-An Chen, New Taipei (TW); Su-Fung Chiu, Miaoli County (TW); Yung-Chi Chang, Hsinchu County (TW); Nien-Jen Chou, Hsinchu (TW); Ping-Jung Wu, Changhua County (TW); Shaw-Hwa Parng, Kaohsiung (TW); Pei-Shin Jiang, Hsinchu (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 855 days.

(21) Appl. No.: 16/727,057

(22) Filed: Dec. 26, 2019

(65) Prior Publication Data
US 2020/0208096 A1 Jul. 2, 2020

Related U.S. Application Data

(60) Provisional application No. 62/785,265, filed on Dec. 27, 2018.

(51) Int. Cl.
*C12M 1/34* (2006.01)
*C12M 1/00* (2006.01)
(Continued)

(52) U.S. Cl.
CPC ............ *C12M 41/46* (2013.01); *C12M 23/08* (2013.01); *C12M 27/00* (2013.01); *C12M 29/00* (2013.01); *C12M 41/26* (2013.01)

(58) Field of Classification Search
None
See application file for complete search history.

(56) References Cited

U.S. PATENT DOCUMENTS 5,707,868 A * 1/1998 Boulay .................. C12M 25/16
435/243
8,980,624 B2 3/2015 Wu et al.
(Continued)

FOREIGN PATENT DOCUMENTS

CN 106085854 A 11/2016
CN 107735491 A 2/2018
(Continued)

OTHER PUBLICATIONS

TW OA issued on Sep. 30, 2020.

*Primary Examiner* — Holly Kipouros
(74) *Attorney, Agent, or Firm* — WPAT, P.C (57) ABSTRACT

A cell culture device includes a culture unit, a gas supply unit, a first pressure unit, at least one inspecting unit and a control unit. The culture unit contains a cell culture liquid. The gas supply unit, connected with the culture unit, is used for transmitting a culture gas into the culture unit. The first pressure unit, connected with the culture unit, is used for applying a pressure to the cell culture liquid in the culture unit. The at least one inspecting unit, connected with the culture unit, is used for receiving the cell culture liquid for inspection. The control unit, electrically coupled with the culture unit, the first pressure unit, the gas supply unit and the at least one inspecting unit, is used for monitoring corresponding condition parameters to determine respective (Continued)

operations. In addition, a cell culture method for the cell culture device is also provided.

5 Claims, 5 Drawing Sheets

(51) Int. Cl.
 *C12M 1/02* (2006.01)
 *C12M 1/24* (2006.01)

(56) References Cited

U.S. PATENT DOCUMENTS

| | | | |
|---|---|---|---|
| 9,783,768 B2 | 10/2017 | Larcher et al. | |
| 2001/0021529 A1* | 9/2001 | Takagi | C12M 21/08 435/395 |
| 2005/0048643 A1* | 3/2005 | Takagi | C12M 27/00 435/284.1 |
| 2006/0275896 A1* | 12/2006 | Anderson | C12M 23/54 435/303.1 |
| 2009/0209035 A1* | 8/2009 | Watanabe | C12M 35/04 435/395 |
| 2010/0203620 A1* | 8/2010 | Grimaldi | C12M 35/02 435/286.7 |
| 2013/0344596 A1 | 12/2013 | Grieshober, Jr. et al. | |
| 2014/0038258 A1* | 2/2014 | Akra | C12M 35/02 435/297.1 |
| 2017/0037369 A1* | 2/2017 | Ramsborg | C12N 5/10 |
| 2018/0298324 A1* | 10/2018 | Takeda | G01N 15/1484 |
| 2021/0123010 A1* | 4/2021 | Gebauer | C12M 41/06 |

FOREIGN PATENT DOCUMENTS

| | | |
|---|---|---|
| CN | 108570417 A | 9/2018 |
| TW | I270576 | 1/2007 |
| TW | M557264 | 3/2018 |

* cited by examiner

FIG. 5

CELL CULTURE DEVICE AND METHOD THEREOF

CROSS REFERENCE TO RELATED APPLICATION

This application claims the benefits of U.S. Provisional application Ser. No. 62/785,265, filed on Dec. 27, 2018, the disclosures of which are incorporated by references herein in its entirety.

TECHNICAL FIELD

The present disclosure relates in general to a cell culture device and a method of the cell culture device.

BACKGROUND

According to various surveys, cancers have been ranked the first of top 10 causes of death worldwide. With medical knowledge grows and accumulates, cancer therapies or treatments are also improved day by day, and new therapy methods have been introducing to the market, from conventional surgeries to chemotherapy, radiotherapy, targeted therapy and recent immunotherapy.

In particular, since the immunotherapy can focus at specific cancer cells to execute unique attacks with less side effects. According to various international publications and reports, about half of the patients can be stabilized and have better chances to survive. In addition, around 70% of the patients can improve life quality. Thus, majority of medical organizations worldwide have devoted intensively to study on the improvement of the immunotherapy.

Nevertheless, the immunotherapy is anyway one of expensive treatments, and thus less popular than the conventional cancer therapies. Hence, in studying the immunotherapy, the improvement upon the cell culture time and quality without increasing therapy cost is definitely crucial and important to the skills in the art.

Accordingly, an improved cell culture device that can increase cell proliferation in both number and viability, and further shorten the cell culture duration, such that the cell culture can be improved and optimized, is definitely welcome and urgent to the skills in the art.

SUMMARY

In one embodiment of this disclosure, a cell culture device includes a culture unit, a gas supply unit, a first pressure unit, at least one inspecting unit and a control unit. The culture unit contains a cell culture liquid. The gas supply unit, connected with the culture unit, is used for transmitting a culture gas into the culture unit. The first pressure unit, connected with the culture unit, is used for applying a pressure to the cell culture liquid in the culture unit. The at least one inspecting unit, connected with the culture unit, is used for receiving the cell culture liquid for inspection. The control unit, electrically coupled with the culture unit, the first pressure unit, the gas supply unit and the at least one inspecting unit, is used for monitoring corresponding condition parameters to determine respective operations.

In another embodiment of this disclosure, a cell culture method includes the steps of: transmitting the cell culture liquid into the culture unit; transmitting the culture gas into the culture unit by the gas supply unit; applying a pressure to the cell culture liquid in the culture unit by the first pressure unit; and, receiving the cell culture liquid for inspection by the at least one inspecting unit.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
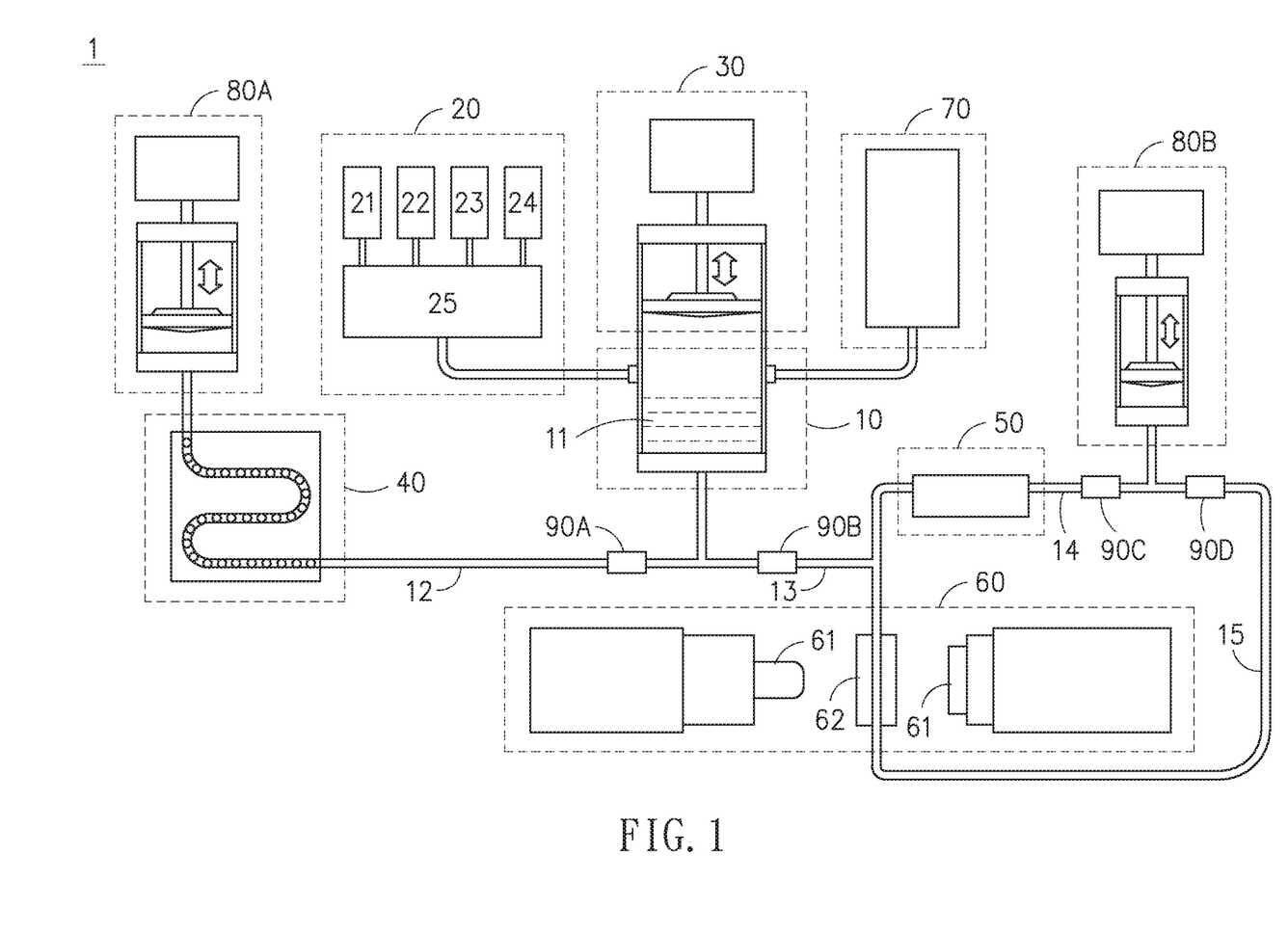
FIG. 1 is a schematic framework of an embodiment of the cell culture device in accordance with this disclosure.

Referring now to FIG. 1, a schematic framework of an embodiment of the cell culture device in accordance with this disclosure is shown. In this embodiment, the cell culture device 1 mainly includes a culture unit 10, a gas supply unit 20, a first pressure unit 30, a magnetic-bead separation unit 40, an acidity-inspecting unit 50 and a viability-inspecting unit 60. All of the culture unit 10, the gas supply unit 20, the first pressure unit 30, the magnetic-bead separation unit 40, the acidity-inspecting unit 50 and the viability-inspecting unit 60 are connected to a control unit (not shown in the figure), such that the control unit can monitor condition parameters related to each of the aforesaid units and further control operation of each of the aforesaid units.

The culture unit 10 is used for containing a cell culture liquid 11. The cell culture liquid 11 is not limited to any specific solution, but is determined up to the purpose of the culturing. For example, the cell culture liquid 11 can be a mixture solution having T cells (one type of lymphocytes) and the other components that is helpful to cultivate the cells.

The culture unit 10 is connected with a culture-liquid transmitting unit 70, in which the culture-liquid transmitting unit 70 is used for transmitting the cell culture liquid into the culture unit 10.

The gas supply unit 20 is connected with the culture unit 10, and used for transmitting a culture gas into the culture unit 10. The determination of the culture gas is dependent on the cells to be cultivated, and is charged into the culture unit 10 to help the cells to grow, such as $N_2$, $O_2$, $CO_2$, fresh air or at least a mixture gas having at least two of aforesaid gases. In this embodiment, the gas supply unit 20 includes a plurality of gas bottles 21~24 and a gas mixer 25. In this embodiment, the gas bottles 21~24 can contain different gases such as the aforesaid $N_2$, $O_2$, $CO_2$ and fresh air.

Through the control unit to evaluate practical needs, at least one gas can be inputted to the culture unit 10 via the gas mixer 25. Alternatively, different gases can be sent into the gas mixer 25 so as to produce by mixing a culture gas according to predetermined percentages, and then this culture gas can be provided to the culture unit 10.

The gas supply unit 20 is used to provide necessary gas into the culture unit 10, so that cells in the cell culture liquid 11 can be better grown. Thereupon, inside the culture unit 10, a positive environment for cultivating the cells can be formed. Simultaneously, according to different percentages, different gases can be mixed together so as to produce a mixture relevant for fulfilling an optimal acidity to the cell culture liquid 11.

The first pressure unit 30, connected with the culture unit 10, is used for applying a pressure to the cell culture liquid in the culture unit 10. This first pressure unit 30 can be, but not limited to, one of a piston and a pump. The choice of the first pressure unit 30 mainly depends on practical requirements. In this embodiment, the first pressure unit 30 is a piston.

The pressure provided by the first pressure unit 30 can be a positive pressure or a negative pressure. With the first pressure unit 30 as a piston in this embodiment, when the piston (not labeled in the figure) of the first pressure unit 30 is pressed downward to increase the pressure upon the culture unit 10, a positive pressure would be applied to the cell culture liquid 11. On the other hand, when the piston of the first pressure unit 30 goes upward, a negative pressure would be applied to the cell culture liquid 11. In this embodiment, the control unit controls the operation of the first pressure unit 30.

The magnetic-bead separation unit 40, connected with the culture unit 10, is used for receiving or sampling the cell culture liquid 11 in the culture unit 10, and for performing magnetic bead separation upon the cell culture liquid 11 having activated magnetic beads.

The acidity-inspecting unit 50, connected with the culture unit 10, is used for receiving or sampling the cell culture liquid 11 in the culture unit 10, and for performing solution acidity inspection upon the cell culture liquid 11.

The viability-inspecting unit 60, connected with the culture unit 10, is used for receiving or sampling the cell culture liquid 11 in the culture unit 10, and for performing cell viability inspection upon the cell culture liquid 11. The viability-inspecting unit 60 is usually consisted of a high-magnification camera 61 and an inspection area 62. The camera 61 inspects the cell culture liquid 11 within the inspection area 62 so as to determine the cell viability.

With the magnetic-bead separation unit 40, the acidity-inspecting unit 50 and the viability-inspecting unit 60 to feedback corresponding examination results of the cell culture liquid 11 to the control unit, the control unit can thus judge these examination results to determine or vary the corresponding condition parameters. For example, the control unit controls the gas supply unit 20 to supply more culture gas, or controls the first pressure unit 30 to apply an additional pressure.

It shall be explained that, according to required examination items, the culture unit 10 is not limited to connect the magnetic-bead separation unit 40, the acidity-inspecting unit 50 and the viability-inspecting unit 60. In some other embodiments, the culture unit 10 may optionally connect at least one of the connects magnetic-bead separation unit 40, the acidity-inspecting unit 50 and the viability-inspecting unit 60, or connect another inspecting unit to perform another examination item. In the case that the cell culture liquid 11 does not have the activated magnetic beads, then the magnetic-bead separation unit 40 would be unnecessary.

In this embodiment, the magnetic-bead separation unit 40, the acidity-inspecting unit 50 and the viability-inspecting unit 60 are connected with second pressure units 80A, 80B, In this embodiment, the second pressure unit 80A, 80B are both in the piston form. With the control unit to control the pistons of the second pressure units 80A, 80B to go up or down, a positive pressure or a negative pressure would be applied to the cell culture liquid 11 in the magnetic-bead separation unit 40, the acidity-inspecting unit 50 and the viability-inspecting unit 60, for performing pushing or sucking operation, respectively.

It shall be explained that, in this embodiment, only the magnetic-bead separation unit 40 is connected with the second pressure unit 80A, while the acidity-inspecting unit 50 and the viability-inspecting unit 60 are both connected with the same second pressure unit 80B. Alternatively, the acidity-inspecting unit 50 and the viability-inspecting unit 60 can be connected with different second pressure units. Namely, according to this disclosure, connections between the aforesaid units and the second pressure units are not limited to the aforesaid embodiments, but depend upon practical requirements.

To control the flow of the cell culture liquid 11 in the culture unit 10 into the magnetic-bead separation unit 40, the acidity-inspecting unit 50 and the viability-inspecting unit 60 for respective examinations, a plurality of valves 90A~90D are furnished to the piping connecting the culture unit 10 and the magnetic-bead separation unit 40, the acidity-inspecting unit 50 and the viability-inspecting unit 60.

As shown, the valve 90A is disposed at the piping 12 connecting the culture unit 10 and the magnetic-bead separation unit 40, the valve 90B is disposed at the piping 13 connecting the culture unit 10 and both the acidity-inspecting unit 50 and the viability-inspecting unit 60, the valve 90C is disposed at the piping 14 connecting the acidity-inspecting unit 50 and the second pressure unit 80B, and the valve 90D is disposed at the piping 15 connecting the viability-inspecting unit 60 and the second pressure unit 80B.

In this embodiment, the valves 90A~90D are electrically coupled with the control unit. Since the control unit controls the valves 90A~90D to be in an open state or a close state, so as to control the flow between the culture unit 10 and the magnetic-bead separation unit 40, the acidity-inspecting unit 50 and the viability-inspecting unit 60. Simultaneously, the first pressure unit 30 and the second pressure units 80A, 80B are used to control the flow path of the cell culture liquid 11.

Figure 2:
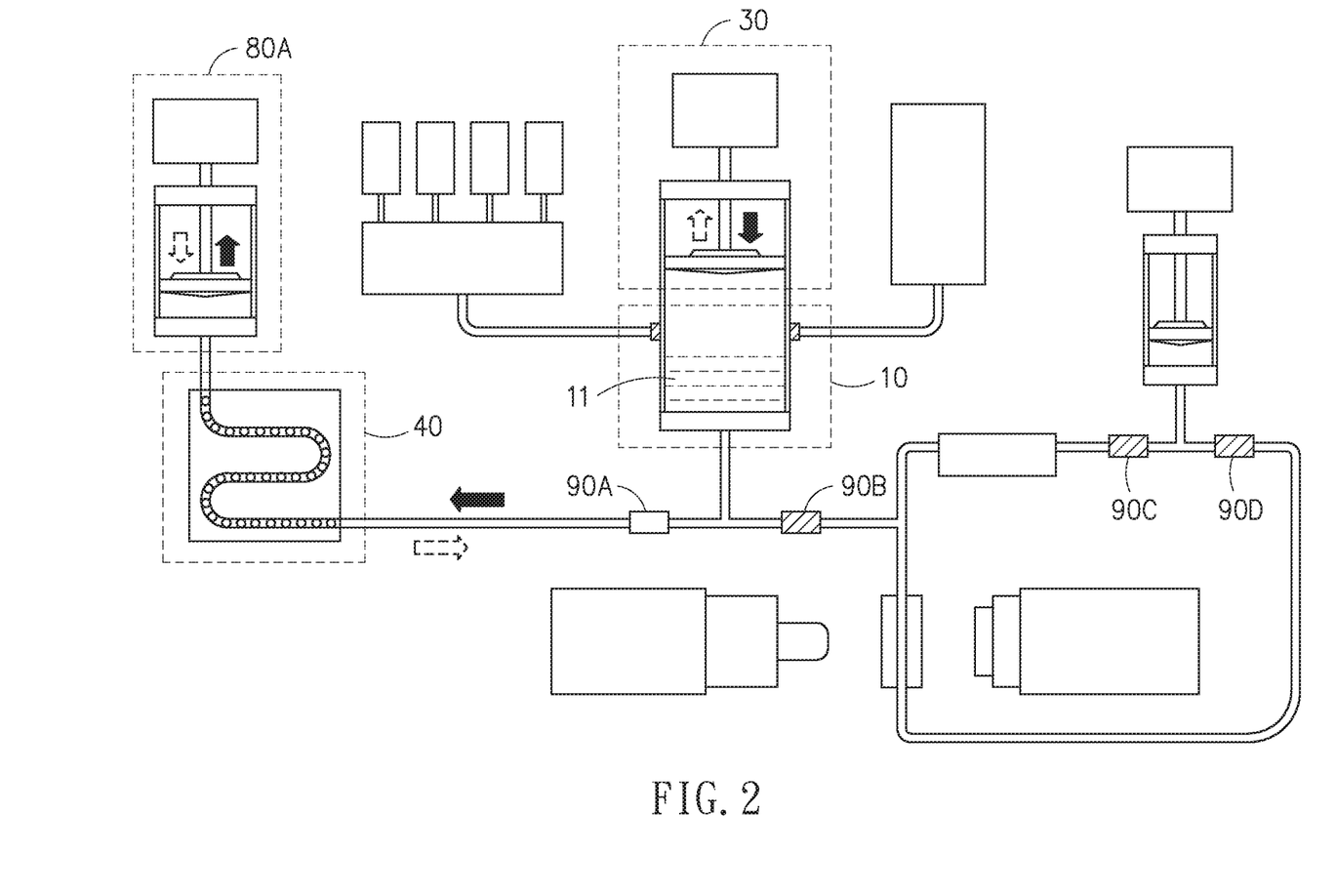
FIG. 2 through FIG. 5 demonstrate different states of FIG. 1, with different degrees of valve openness to show specific connection states of the cell culture device.

Referring now to FIG. 2, while in performing the magnetic bead separation, the valve 90A is in the open state, and the other valves 90B~90D are in the close state (symbolize by hatched lines in the valves 90B~90D). Thereupon, the second pressure unit 80A is controlled to go up so as to provide a negative pressure, and the first pressure unit 30 goes down to provide a positive pressure (indicated by a solid black arrow head), such that the cell culture liquid 11 in the culture unit 10 can be pushed into the magnetic-bead separation unit 40 for undergoing the corresponding magnetic bead separation.

After the magnetic bead separation is finished, the first pressure unit 30 is controlled to go up to provide a negative pressure, and the second pressure unit 80A goes down to provide a positive pressure (indicated by a dashed arrow head), such that the cell culture liquid 11 going through the magnetic bead separation can be pushed from the magnetic-bead separation unit 40 back to the culture unit 10.

Figure 3:
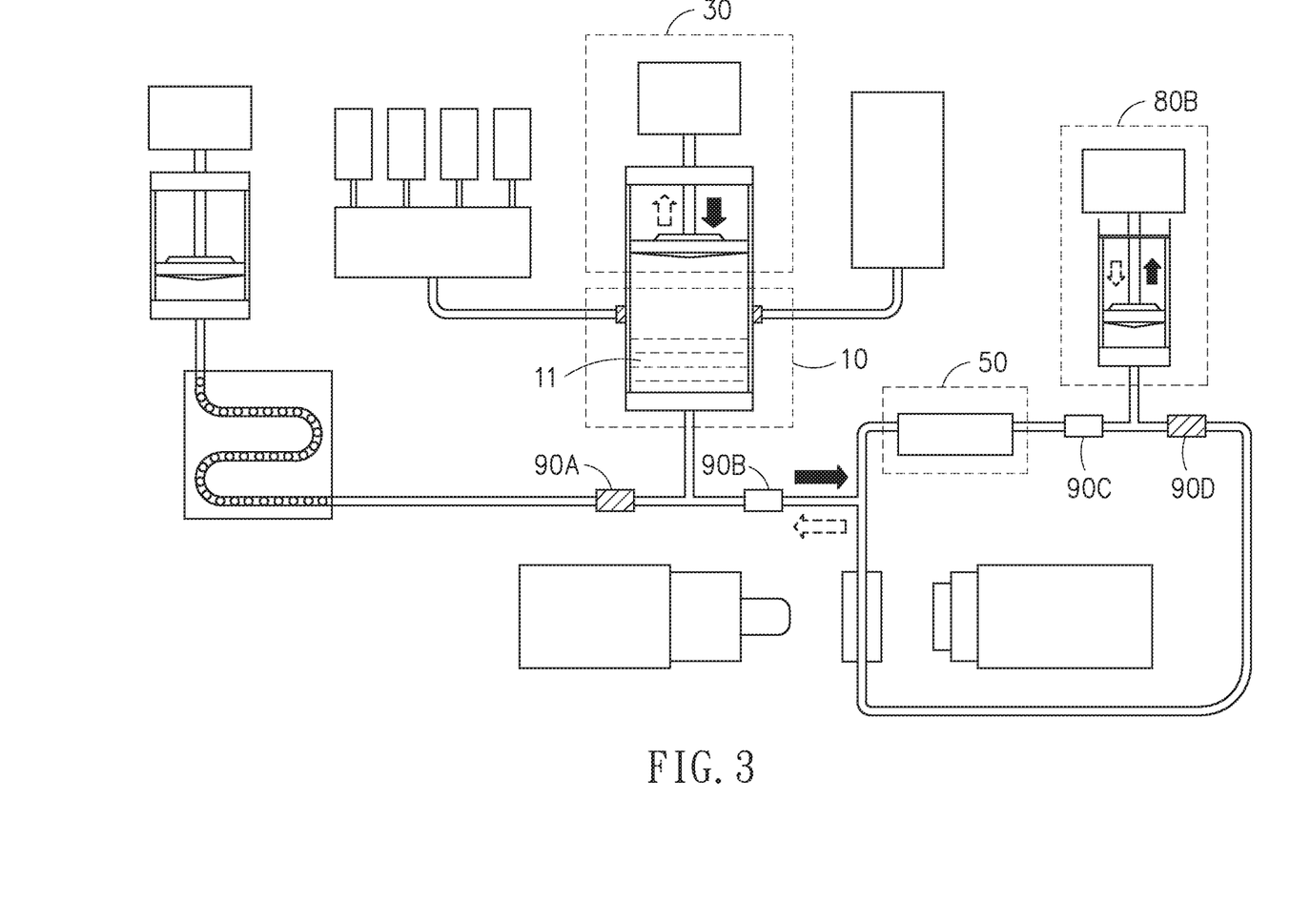

Referring now to FIG. 3, while in performing the solution acidity inspection, the valves 90B, 90C are both in the open state, and the other valves 90A, 90D are in the close state (symbolize by hatched lines in the valves 90A, 90D). Thereupon, the second pressure unit 80B is controlled to go up to provide a negative pressure, and the first pressure unit 30 goes down to provide a positive pressure (indicated by a solid black arrow head), such that the cell culture liquid 11 in the culture unit 10 can be pushed into the acidity-inspecting unit 50 for undergoing the solution acidity inspection.

After the solution acidity inspection is finished, the first pressure unit 30 is controlled to go up to provide a negative pressure, and the second pressure unit 80B goes down to provide a positive pressure (indicated by a dashed arrow head), such that the cell culture liquid 11 going through the solution acidity inspection can be pushed back to the culture unit 10 from the acidity-inspecting unit 50.

Figure 4:
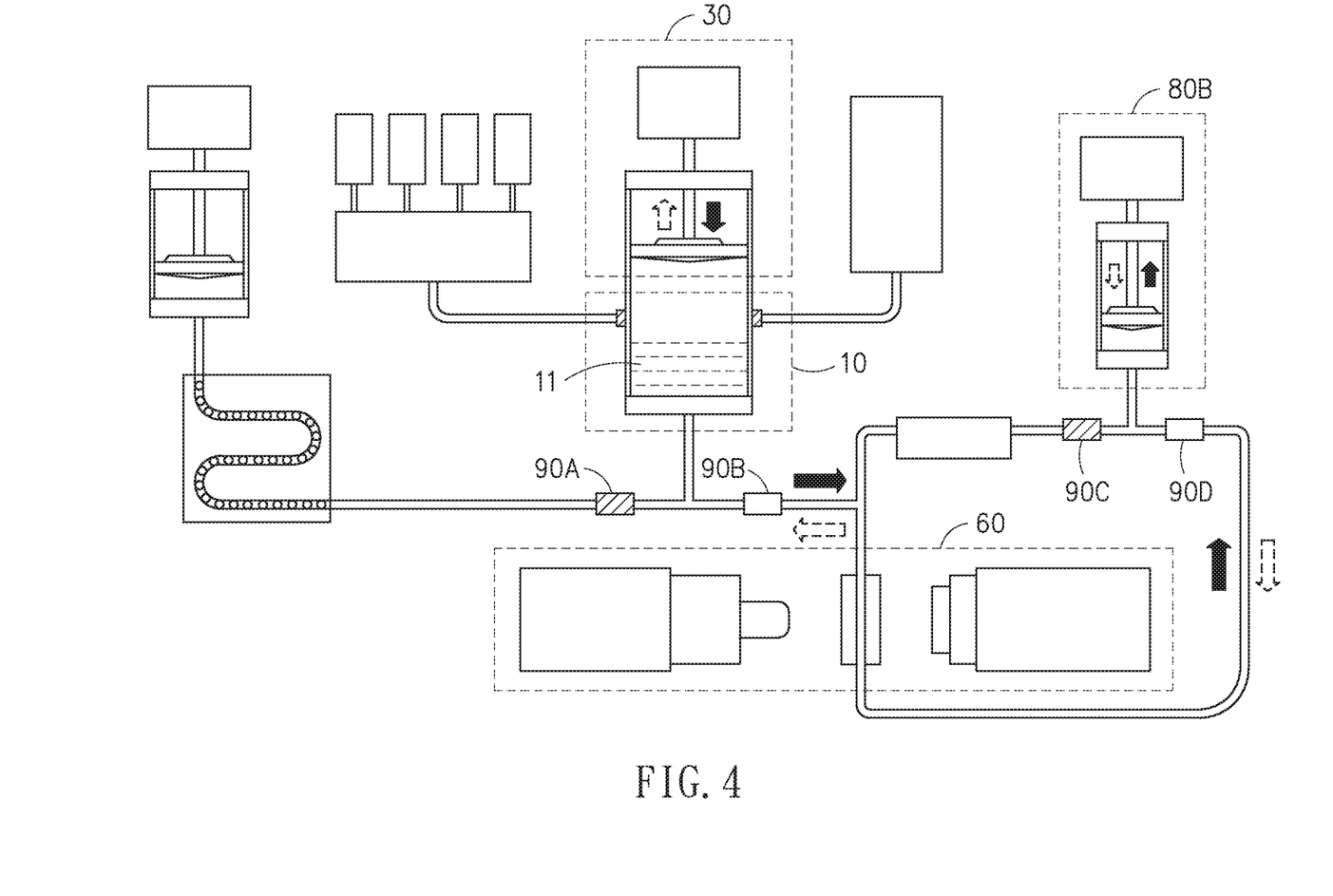

Referring now to FIG. 4, while in performing the cell viability inspection, the valves 90B, 90D are in the open state, and the other valves 90A, 90C are in the close state (symbolize by hatched lines in the valves 90A, 90C). Thereupon, the second pressure unit 80B is controlled to go up to provide a negative pressure, and the first pressure unit 30 goes down to provide a positive pressure (indicated by a solid black arrow head), such that the cell culture liquid 11 in the culture unit 10 would be pushed into the viability-inspecting unit 60 for performing the cell viability inspection.

After the cell viability inspection is finished, the first pressure unit 30 is controlled to go up to provide a negative pressure, and the second pressure unit 80B goes down to provide a positive pressure (indicated by a dashed arrow head), such that the cell culture liquid 11 going through the cell viability inspection can be pushed from the viability-inspecting unit 60 back to the culture unit 10.

It shall be explained that, if the cell culture liquid sent to the magnetic-bead separation unit 40, the acidity-inspecting unit 50 or the viability-inspecting unit 60 needn't be recycled back to the culture unit 10 after the respective examinations, the existence of the second pressure units 80A, 80B would be unnecessary. In other words, since the second pressure units 80A, 80B is purposely to push the cell culture liquid 11 back to the culture unit 10, thus the second pressure units 80A, 80B can be removed if the cell culture liquid needn't be recycled back to the culture unit 10.

Figure 5:
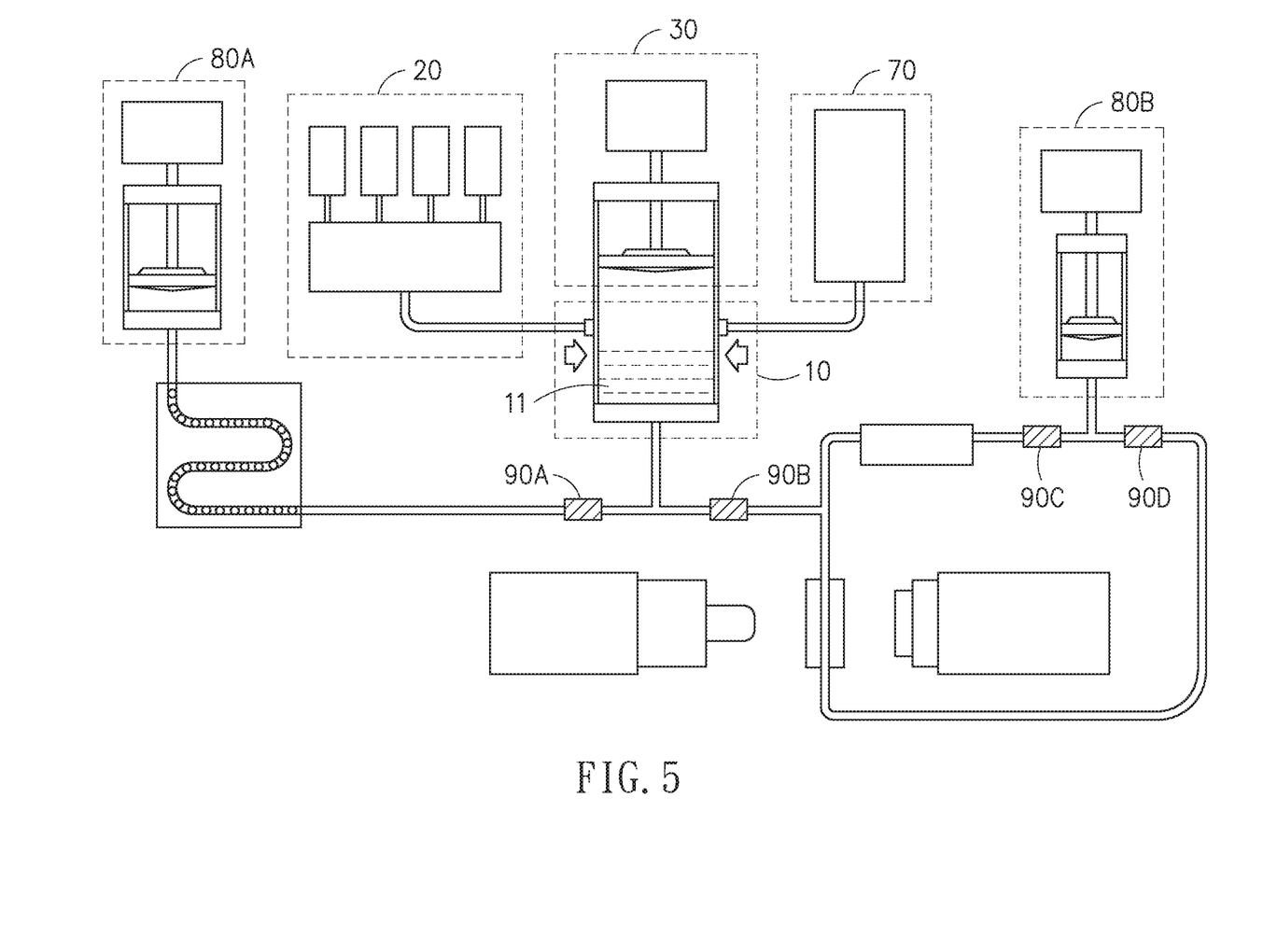

Referring now to FIG. 5, when at least the valves 90A~90D are in the close state (symbolize by hatched lines in the valves 90A~90D), and the first pressure unit 30 and the second pressure units 80A, 80B are all in the silent state, then the culture-liquid transmitting unit 70 is used for transmitting the cell culture liquid into the culture unit 10, or the gas supply unit 20 is further introduced to supply the culture gas to the culture unit 10.

Referring back to FIG. 1, based on the cell culture device 1 of this disclosure, a corresponding cell culture method includes the following steps:

(A) Transmit the cell culture liquid 11 into the culture unit 10;

(B) Transmit the culture gas into the culture unit 10 by the gas supply unit 20;

(C) Apply a pressure to the cell culture liquid 11 in the culture unit 10 by the first pressure unit 30; and (D) Receive the cell culture liquid 11 for inspection by at least one of the magnetic-bead separation unit 40, the acidity-inspecting unit 50 and the viability-inspecting unit 60.

In summary, in the cell culture device and the method of the cell culture device provided by this disclosure, the first pressure unit is used to apply a positive pressure to the cell culture liquid in the culture unit so as to promote gas-and-liquid exchange and cell growth in the culture unit. In addition, with the magnetic-bead separation unit, the acidity-inspecting unit and the viability-inspecting unit to inspect the condition of the cell culture liquid, the cell culture liquid of this disclosure can be maintained at an optimal state for growing the cells, such that the entire cell culture duration can be shortened, and the cell culture process can be improved and optimized.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A cell culture device, comprising:
a culture unit, for containing a cell culture liquid and cultivating cells, wherein the culture unit has a first end and a second end with the first end located on an opposite side of the second end;
a gas supply unit, connected with the culture unit, used for transmitting a culture gas into the culture unit;
a first pressure unit, connected with the culture unit via the first end, used for applying a positive or a negative pressure to the cell culture liquid in the culture unit;
at least one cell culture inspecting unit, having a third end and a fourth end with the third end located on an opposite side of the fourth end, connected with the culture unit via at least one pipe, wherein the third end of the at least one cell culture inspecting unit is connected with the second end of the culture unit, wherein each of the at least one cell culture inspecting unit includes an inspection area for receiving the cell culture liquid, wherein each of the at least one cell culture inspecting unit inspects a property of the cell culture liquid received;
a second pressure unit, connected with the at least one cell culture inspecting unit via the fourth end, wherein the second pressure unit is to apply a positive pressure or a negative pressure to the cell culture liquid in the at least one cell culture inspecting unit;
a control unit, electrically coupled with the culture unit, the first pressure unit, the gas supply unit and the at least one cell culture inspecting unit, used for monitoring corresponding condition parameters to determine respective operations; and
a plurality of valves disposed between the culture unit and the at least one cell culture inspecting unit, the plurality of valves being electrically connected with the control unit, the control unit controlling the plurality of valves to be in one of an open state and a close state so as to control flow between the culture unit and the at least one cell culture inspecting unit;
wherein when the first pressure unit apply a positive pressure to the cell culture liquid in the culture unit, the second pressure unit apply a negative pressure to the cell culture liquid in the at least one cell culture inspecting unit such that the cell culture liquid is pushed into the at least one cell culture inspecting unit from the culture unit; and wherein when the first pressure unit apply a negative pressure to the cell culture liquid in the culture unit, the second pressure unit apply a positive pressure to the cell culture liquid in the at least one cell culture inspecting unit such that the cell culture liquid is pushed into the culture unit from the at least one cell culture inspecting unit.

2. The cell culture device of claim 1, wherein the first pressure unit is one of a piston and a pump.

3. The cell culture device of claim 1, wherein the gas supply unit includes:

a plurality of gas bottles, each of the plurality of gas bottles being used for containing a gas; and a gas mixer, connected with the plurality of gas bottles, used for receiving at least two gases to form the culture gas.

4. The cell culture device of claim 3, wherein the gas is one of $N_2$, $O_2$, $CO_2$ and fresh air.

5. The cell culture device of claim 1, wherein the at least one cell culture inspecting unit is at least one of a magnetic-bead separation unit, an acidity-inspecting unit and a viability-inspecting unit.

* * * * *